United States Patent
Cobanoglu et al.

(10) Patent No.: US 11,886,627 B2
(45) Date of Patent: Jan. 30, 2024

(54) MOTION CAPTURING GARMENTS AND SYSTEM AND METHOD FOR MOTION CAPTURE USING JEANS AND OTHER GARMENTS

(71) Applicant: Sanko Tekstil Isletmeleri San. Ve Tic. A.S., Inegol-Bursa (TR)

(72) Inventors: Ozgur Cobanoglu, Inegol-Bursa (TR); Jitka Eryilmaz, Inegol-Bursa (TR); Serkan Mert, Inegol-Bursa (TR); Fehim Caglar, Inegol-Bursa (TR)

(73) Assignee: SANKO TEKSTIL ISLETMELERI SAN. VETIC. A.S., Inegol-Bursa (TR)

( * ) Notice: Subject to any disclaimer, the term of this patent is extended or adjusted under 35 U.S.C. 154(b) by 931 days.

(21) Appl. No.: 15/654,789

(22) Filed: Jul. 20, 2017

(65) Prior Publication Data
US 2018/0024622 A1 Jan. 25, 2018

(30) Foreign Application Priority Data
Jul. 21, 2016 (EP) .................................... 16180659

(51) Int. Cl.
*G06F 3/01* (2006.01)
*A61B 5/11* (2006.01)
(Continued)

(52) U.S. Cl.
CPC .............. *G06F 3/011* (2013.01); *A41D 1/005* (2013.01); *A41D 1/06* (2013.01); *A61B 5/112* (2013.01);
(Continued)

(58) Field of Classification Search
CPC ...... G06F 3/011; G06F 3/0346; A61B 5/1118; A61B 5/112; A61B 5/1121; A61B 5/6804;
(Continued)

(56) References Cited

U.S. PATENT DOCUMENTS

| | | | |
|---|---|---|---|
| 2,143,649 A | * | 10/1939 | Dansard ................... H01B 7/06 174/69 |
| 2001/0050645 A1 | | 12/2001 | Boyle |

(Continued)

FOREIGN PATENT DOCUMENTS

| | | |
|---|---|---|
| JP | 2012214968 | 11/2012 |
| WO | 2010120945 | 10/2010 |

(Continued)

OTHER PUBLICATIONS

Salehi et al., 2014 4th International Conference on Wireless Mobile Communication and Healthcare—Transforming Healthcare Through Innovations in Mobile and Wireless Technologies (MobiHealth) (Year: 2014).*

(Continued)

*Primary Examiner* — Jacqueline Cheng
*Assistant Examiner* — Tho Q Tran

(57) ABSTRACT

A real-time motion capture system and garment includes a wearable activity monitor that may be a pair of denim jeans. The wearable activity monitor includes multiple sensors such as accelerometers, gyrometers, magnetometers disposed within the seams of the garment. A microprocessor and wireless transmitter) communicate the motion data to an external device. The microprocessor and wireless transmitter may be included within one of the seams. An elastically stretchable ribbon or a flexible ribbon such as a kapton ribbon or a ribbon formed of textile, electrically couples the sensors and microprocessor and is also disposed inside the seams and the components within the seam are coated with a waterproof coating. The external device can store the data or display and analyze the data real-time, and may communicate the data to a further electronic device.

6 Claims, 9 Drawing Sheets

(51) Int. Cl.
| | |
|---|---|
| *A41D 1/06* | (2006.01) |
| *A41D 1/00* | (2018.01) |
| *A61B 5/00* | (2006.01) |
| *G06F 3/0346* | (2013.01) |
| *H04W 4/02* | (2018.01) |
| *G06T 7/20* | (2017.01) |

(52) U.S. Cl.
CPC ........... *A61B 5/1118* (2013.01); *A61B 5/1121* (2013.01); *A61B 5/6804* (2013.01); *H04W 4/025* (2013.01); *A61B 2562/028* (2013.01); *A61B 2562/0219* (2013.01); *A61B 2562/043* (2013.01); *G06F 3/0346* (2013.01); *G06T 7/20* (2013.01)

(58) Field of Classification Search
CPC ........ A61B 2562/043; A61B 2562/028; A61B 2562/0219; A41D 1/06; A41D 1/005; H04W 4/025; G06T 7/20
USPC ......................................................... 600/595
See application file for complete search history.

(56) References Cited

U.S. PATENT DOCUMENTS

| | | |
|---|---|---|
| 2007/0299325 A1 | 12/2007 | Farrell et al. |
| 2008/0215974 A1* | 9/2008 | Harrison ................. A63F 13/42 715/706 |
| 2009/0193689 A1* | 8/2009 | Galica ................... A43B 3/0005 36/137 |
| 2010/0012122 A1 | 1/2010 | Shaffer et al. |
| 2010/0121227 A1* | 5/2010 | Stirling et al. ....... A61B 5/1124 600/595 |
| 2011/0077497 A1 | 3/2011 | Oster |
| 2012/0029299 A1 | 2/2012 | Deremer et al. |
| 2012/0136231 A1 | 5/2012 | Markel |
| 2012/0246795 A1* | 10/2012 | Scheffler .............. A61B 5/0205 2/243.1 |
| 2014/0007095 A1 | 1/2014 | Campion et al. |
| 2014/0070957 A1 | 3/2014 | Longinotti-Buitoni et al. |
| 2014/0296651 A1 | 10/2014 | Stone |
| 2014/0318699 A1* | 10/2014 | Longinotti-Buitoni ..................... A41D 1/002 156/247 |
| 2015/0231403 A1 | 8/2015 | Kaib et al. |
| 2015/0272482 A1 | 10/2015 | Houmanfar et al. |
| 2016/0150362 A1 | 5/2016 | Shapiro et al. |
| 2016/0174840 A1 | 6/2016 | Udoh et al. |
| 2016/0202755 A1* | 7/2016 | Connor ................... G06F 3/011 73/865.4 |
| 2016/0245665 A1* | 8/2016 | Logan ..................... G01W 1/00 |
| 2016/0270700 A1* | 9/2016 | Baxi ..................... A61B 5/1121 |
| 2018/0303383 A1* | 10/2018 | Connor ................... G06F 3/014 |

FOREIGN PATENT DOCUMENTS

| | | |
|---|---|---|
| WO | 2016051268 | 4/2016 |
| WO | 2016118746 | 7/2016 |
| WO | 20170013493 | 1/2017 |

OTHER PUBLICATIONS

European Search Report dated Feb. 23, 2017 for European priority application No. 16180659.1.
International Search Report dated Jan. 23, 2018 for corresponding PCT application No. PCT/EP2017/068201.
European Search Report dated Dec. 5, 2017 for corresponding European application No. 17182026.9.
Office Action issued by the EPO dated Apr. 24, 2019 for corresponding European application No. 17182026.9.
International Preliminary Report on Patentability issued by the EPO dated Jan. 31, 2019 for corresponding International application No. PCT/EP2017/068201.
Official Letter issued by the JPO dated Mar. 16, 2021 for corresponding JP patent application No. 2017-140581.
Office Action issued by the Japanese Patent Office dated Jan. 4, 2022 for corresponding JP patent application No. 2017-140581.

* cited by examiner

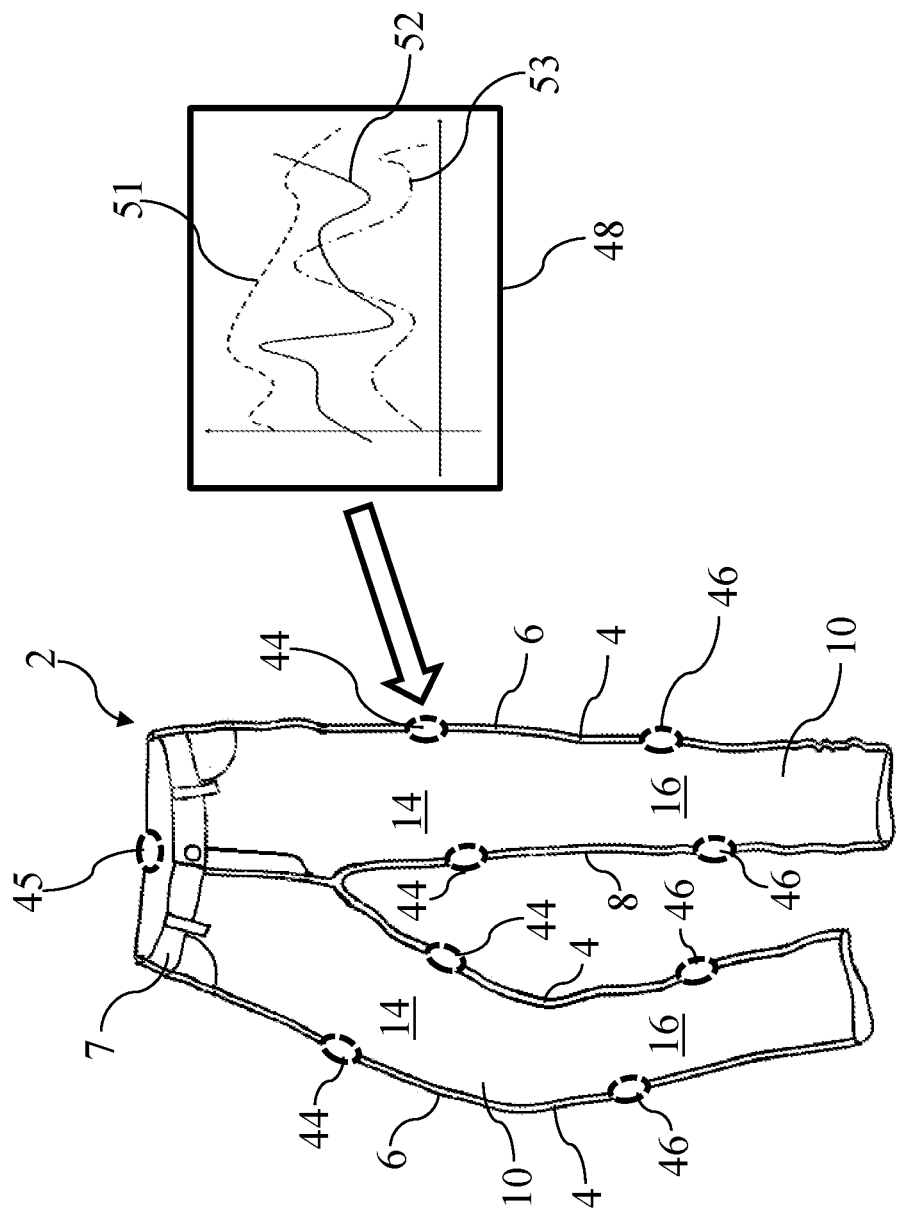

MOTION CAPTURING GARMENTS AND SYSTEM AND METHOD FOR MOTION CAPTURE USING JEANS AND OTHER GARMENTS

RELATED APPLICATION

This application claims priority to European application 16180659.1, filed 21 Jul. 2016, the contents of which are herein incorporated by reference as if set forth in their entirety.

TECHNICAL FIELD

The present invention relates to the field of the motion capture (Mo-cap for short), i.e. the process of recording the movement of objects or people. The present invention can be used in military, entertainment, sports, medical, and various other applications.

BACKGROUND

Motion capture is usually used in sports research, film-making and video game development for recording actions of human actors by means of one or more cameras configured to detect the positions of a plurality of markers attached to the body of the actor at determined points. The markers can be coated with a retroreflective material in order to reflect light that is generated near the cameras lens. Alternatively, the markers can be provided with a light source, e.g. LEDs. The camera's threshold can be adjusted so only the light of markers will be sampled, ignoring skin and fabric of the actor. The movements recorded are thus used to animate digital character models in a 3D environment.

A further technique provides a marker-less approach to motion capture. These systems do not require users to wear markers for tracking. By means of special computer algorithms, it can be possible to analyze multiple streams of optical input and identify human forms, breaking them down into constituent parts for tracking. In the above mentioned systems, one or more cameras are required for detecting and recording the motion of a user. As a result, the motion capturing can be carried out only in a recording studio or in a limited space within the visual range of the camera(s).

Mechanical trackers, comprising rigid or flexible goniometers which are worn by the user, are also known. These angle-measuring devices provide joint angle data to a processor in which kinematic algorithms are used to determine the body position of the user. Conventional mechanical tracking systems suffer from poor accuracy particularly when there are more than one degrees of freedom.

Inertial measurement devices are known for detecting the position of a marker without the need of a camera but are generally used in conjunction with systems that can be used only as motion capture systems, and are generally quite visible, relatively heavy, awkward and usually uncomfortable apparatuses designed for short term use.

Improved motion capture systems and motion capture systems that are easier to use, are needed.

SUMMARY

An object of the present invention is to overcome the drawbacks of the prior art approaches cited above and to provide a motion capture garment, and a motion capture system able to reliably detect the movement of a wearer using a garment that is comfortable to wear and has a stylish appearance.

A further object of the present invention is to provide a motion capture system that is easily assembled onto a garment, and is able to be washed in a reliable manner. These and other objects are achieved by the present invention by means of a garment according to claim 1, by a motion capture system according to claim 12, by a method for monitoring and analyzing motion according to claim 13, and by a motion capture circuit according to claim 18. Various other advantageous aspects of the invention will be indicated in dependent claims.

In particular, according to the present invention, the garment comprises fabric and includes a plurality of inertial measurement units (IMU's) contained within seams of said garment. The IMU's are advantageously configured to detect motion in 360 degrees in all three axes.

This aspect advantageously enables the motion of the wearer to be detected during the daily activity of the user by using a daily garment that is physically comfortable and/or has a stylish appearance.

The garment may further comprise at least one microcontroller disposed on or in the garment and electrically coupled to the plurality of IMU's.

According to an aspect of the present invention, the at least one microcontroller is contained within at least one of the seams.

Some embodiments provide that the garment further comprises at least one of an LED and a vibration member disposed within at least one of the seams. These embodiments allow to provide visual and/or tactile useful information to the user. In various embodiments, the garment is formed of denim and in some embodiments, the fabric may be formed of a stretch denim. According to an aspect of the present invention, the plurality of IMU's includes a plurality of accelerometers. The plurality of IMU's further includes a plurality of gyrometers and a plurality of magnetometers. The plurality of IMU's are in electronic communication with at least one external data receiving and processing device such as a smartphone, a computer or other electronic devices provided with a processor. In various embodiments, the garment further comprises a wireless transmitter disposed in or on the garment and adapted to transmit data from the IMU's to the external data receiving and processing device.

The plurality of IMU's may be electronically coupled to one another along the seams by a ribbon of a flexible material disposed within the seams. The flexible material may be plastic, or textile or conductive yarns. The ribbon may include a plurality of electrical connections (such as conductive traces, wires, electrical cables, and the like) to form a communication bus.

Some embodiments provide that the ribbon is elastically stretchable by at least 10% and that the electrical connections are arranged along the ribbon in a crooked path (i.e. a continuously nonlinear path), such as a wavy or a zigzag path. In other words, by applying a determined force at the ends of the ribbon, the ribbon can be stretched (i.e. deformed by increasing its length) by at least 10%. When the force is removed, the ribbon returns elastically to the original size. The wavy or zigzag or crooked pattern of the electrical connections prevent the connections from breaking when the ribbon is stretched.

These embodiments advantageously enhance the wearing comfort, so that the wearer cannot notice the presence of electronics embedded in the garment when the garment is worn.

According to an aspect of the disclosure, the garment further comprises a waterproof coating on the ribbon and the IMU's, and within the seams. This aspect advantageously provides that the electronic components of the garments are isolated from sweat, water and any other liquid or other fluid such as would be experienced during laundering.

Some embodiments can provide that the garment is a pair of pants. In some such pants embodiments, the seams include, for each pant leg of the pair of pants, an outer lateral seam extending in a longitudinal direction along a wearer's leg and/or an inner medial seam extending in the longitudinal direction along the wearer's leg. Each of the outer lateral seams and/or each of the inner medial seams includes at least one IMU disposed along a wearer's tibia portion, and at least one IMU disposed along a lower portion of the wearer's leg.

In some such pants embodiments, the seams include a waist seam extending the wearer's waist. The waist seam includes at least one IMU that is disposed along the wearer's lower back when worn.

In other embodiments the garment may be an upper body garment such as a shirt of various types and models.

A further object of the present invention is a motion capture system comprising a garment comprising fabric and including a plurality of inertial measurement units (IMU's) contained within seams of the garment, a wireless transmitter or transceiver disposed in or on the garment and adapted to at least transmit data from the IMU's, and an external device including a processor adapted to receive and analyze the transmitted data and a display that displays the data.

The external device may control at least one further electronic device based upon the data.

Some embodiments of the system of the present invention provides that the plurality of IMU's includes at least one accelerometer, at least one gyrometer and at least one magnetometer coupled to one another along the seams by a ribbon of a flexible material with a coating thereon. The coated kapton ribbon further disposed within the seams and, further comprising at least one of an LED and a vibration member coupled to the flexible ribbon in the seam. In some embodiments the IMU's may be islands of electronics connected to each other by elastically stretchable busses, for example textile busses provided with electrical cables arranged in a wavy or zigzag path. The IMU's may be formed on ordinary PCB's and may be coated with coatings such as resins or molded plastics.

The system may advantageously include at least one microcontroller disposed within the seams, the plurality of IMU's electrically coupled to another and to the microcontroller by a ribbon of a flexible material with a coating thereon, the coated ribbon further disposed within the seams.

Another object of the present invention is to provide a method for monitoring and analyzing motion in real time, the method comprising:
acquiring motion data from a plurality of inertial measurement units (IMU's) disposed within seams of a garment disposed on a non-stationary entity;
and at least one of displaying and analyzing the data.

According to an aspect of the present invention, the method further comprises at least one microcontroller disposed within one of the seams wirelessly transmitting the data to a device that includes at least one of a processor and a display, wherein the at least one of displaying and analyzing includes analyzing motion data regarding angle, yaw, pitch, location and acceleration of each of a human wearer's femurs, tibias and fibulas.

Some embodiments can provide that the method further comprises the step of detecting the gravity vector by means of at least one IMU (e.g., an IMU arranged within a seam of the garment disposed along the wearer's waist). In these embodiments the step of acquiring motion data is carried out using the gravity vector as reference.

The method step of acquiring motion data may include acquiring the motion data from an accelerometer, a gyrometer and a magnetometer. The method may include analyzing the data using an algorithm applying linear quadratic estimation methods.

Some embodiments can provide that the method further comprises controlling at least one electronic device using the data. In some embodiments, the at least one of displaying and analyzing the data includes visually displaying movement associated with the motion data on a visual display.

Some embodiments can provide that the method comprises the step of collecting the motion data during a collection period and displaying the collected data when desired. The step of displaying the collected motion data may include displaying the statistic distribution (for example the histogram) of the angles for each human wearer's femur and for each human wearer's tibias or fibulas.

A further object of the present invention is a motion capture circuit comprising a ribbon of a flexible material, comprising a plurality of electrical connections forming a communication bus, a plurality of inertial measurement units (IMU's) coupled to one another by the ribbon, a microcontroller electrically connected to the IMU's, and a wireless transmitter adapted to wirelessly transmit data from the IMU's to at least one external data receiving and processing device. In various embodiments, the ribbon is elastically stretchable by at least 10%, and the electrical connections are arranged along the ribbon in a wavy, zigzag, or other crooked path.

Advantageously, the circuit further comprises a waterproof coating, the IMU's and the ribbon are coated with the waterproof coating that is produced by a low pressure molding process. The waterproof coating is applied after the electrical cables of the ribbon are connected to the IMU's, so that the waterproof coating covers and seals the whole IMU and the end portions of the ribbon, where the bus is connected to the IMU's.

According to a particular aspect of the present invention, the ribbon is conformed to be contained within seams of a garment.

According to some embodiments the circuit may include one or more batteries, for example rechargeable batteries.

BRIEF DESCRIPTION OF THE DRAWING

The present invention is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawing.

FIG. 1A provides an expanded view of a portion of the garment shown in FIG. 1.

FIGS. 4A-4C show various arrangements for locating sensors on the wearable activity monitor garments according to various embodiments of the disclosure.

DETAILED DESCRIPTION

Figure 1:
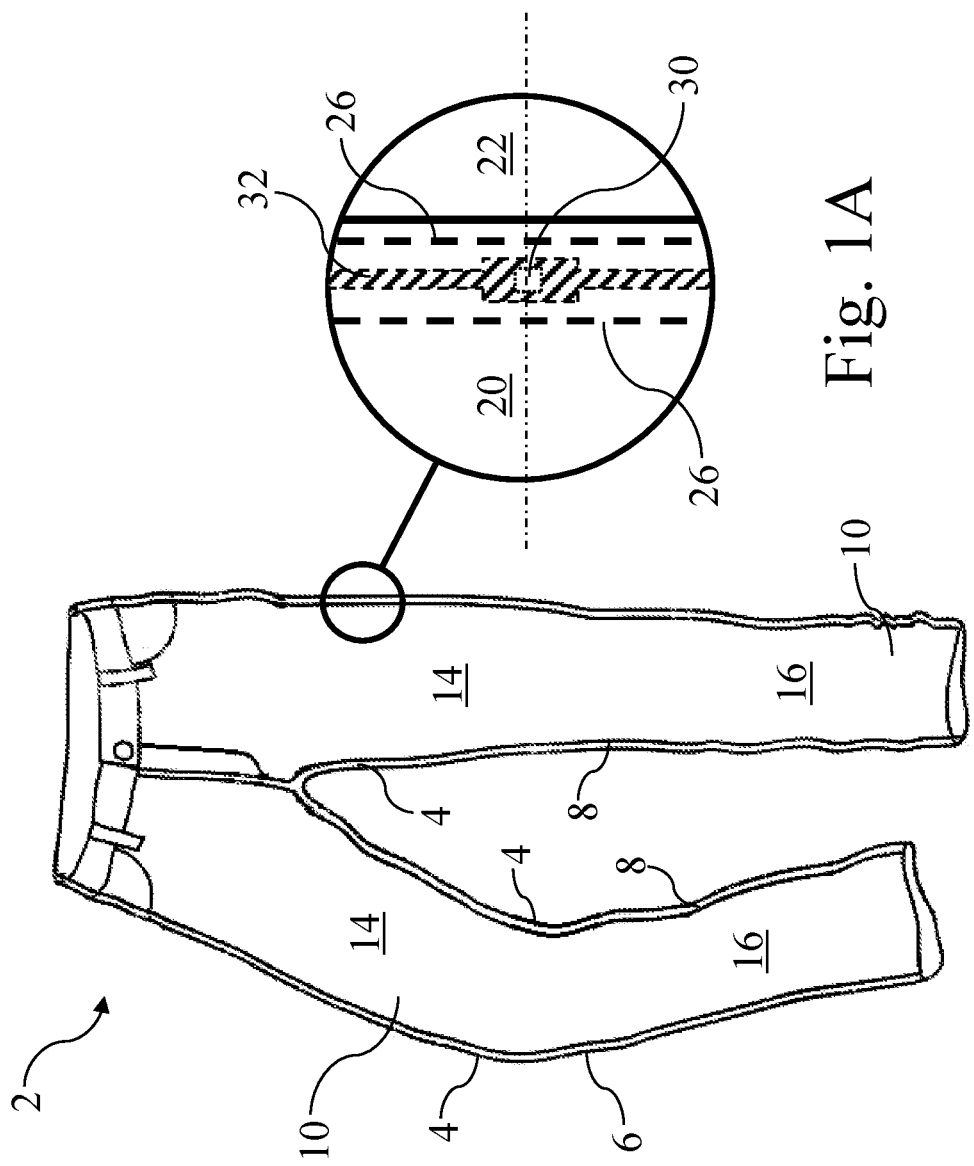
FIG. 1 shows a wearable activity monitor garment according to various embodiments of the disclosure.

The present disclosure provides a real-time motion capture system and garment. The garment is a wearable activity monitor and may be a shirt or a pair of jeans or any of various other garments and may be formed of denim or other suitable materials. The wearable activity monitor includes multiple sensors such as inertial measurement units, IMU's. The multiple inertial measurement units include accelerometers, gyrometers, magnetometers and other sensors. The IMU's are in electronic communication with one another and at least one microcontroller and also with one or more external data receiving and processing devices. The IMU's are advantageously all disposed within the seams of the garment. Stated alternatively, the IMU's are contained inside the seams formed between pieces of fabric, in the garment. A microprocessor may be included within one of the seams or at another location in or on the garment. A tactile notification device and/or an LED may also be included within one of the seams, in various embodiments. Ribbons formed of flexible material such as textile or plastic or conductive yarns, electrically couple the IMU's and microprocessor and any other devices, and are also disposed inside the seams to provide a true wearable activity tracker with the flexible circuit boards and the IMU's contained within the seams. The ribbon may be a flexible circuit board such as a kapton ribbon and may be advantageously coated with a waterproof coating as may be the other electronic components within the seam.

The motion data obtained by the IMU's may be wirelessly transmitted to an external data receiving and processing device such as a computer or other processor, by a wireless transmitter such as a radio antenna configured to transmit data generated by the IMU's. The wireless transmitter is disposed on or in the garment and may be part of the microprocessor. The disclosure provides a wearable activity tracker that is attractive, comfortable, fashionable, non-obstructive, lightweight and washable. No cables are required outside of the garment, the connections are invisible and the routing is not visible because the components are disposed within the seams where they are coated and thus isolated from sweat, water and any other liquid or other fluid.

The wearable activity monitor finds application in the fields of medicine, physical therapy and rehabilitation, sports coaching, sports performance analysis, body figure recording, posture and balance monitoring, sports injury prevention, differential analysis of walking and running, monitoring synchronized motions of groups of people, gait analysis for running and walking, throwing motion analysis, monitoring the activities of the elderly, sleep apnea analysis through body movement during sleep, and in various other fields.

The IMU's may be positioned in the seams and the seams positioned relative to a wearer's body so as to use the accelerometers, gyrometers and magnetometers to capture motion on a real-time basis by measuring the exact angle, yaw, location and pitch of body parts as well as the acceleration and other movements of the body parts. The IMU's are advantageously configured to detect motion in 360 degrees in all three axes. Multiple accelerometers may be utilized in a complementary fashion in cases in which accelerometers with limited ranges are used, to cover dead angles.

For example, and as will be shown in the drawings, the garments may be a pair of pants and include, for each pant leg, an outer lateral seam extending in a direction parallel a wearer's leg bones and an inner medial seam extending along the direction parallel a wearer's leg bones. Each of the outer lateral and inner medial seams may include each of an accelerometer, a gyrometer and a magnetometer disposed both along a wearer's upper leg (femur) portion and all three of an accelerometer, a gyrometer and a magnetometer also disposed along the wearer's lower leg (tibia and fibula) portion to measure and monitor each bone of the wearer's leg. As above, in some embodiments described herein, multiple accelerometers may be utilized in a complementary fashion.

The disclosure also provides an activity tracking system. The system includes the wearable motion-capturing garment as above and a wireless transmitter such as a radio antenna, disposed in or on the garment and adapted to transmit data from the IMU's to an external device. The external device may include a processor and a display. The external device may include a memory for storing the data. The display may visually display, on a screen or other visible interface such as a graphical user interface (GUI), the motion of multiple persons wearing the garments. The processor analyzes the data received from all of the IMU's. In some embodiments, the external device provides feedback messages or an alarm and in some embodiments, the external device sends a signal to another electronic device based on the data analysis. In some embodiments, the system also includes the garment acting as a controller to control other electronic devices such as home appliances, computer games, Xbox, other electronic devices and so forth. The data obtained from the IMU's is provided to a controller that, in turn, controls electronic devices such as the aforementioned examples.

The disclosure also provides a method for real time motion capture and the analysis of such motion. The method includes obtaining data from a wearable activity monitor such as the garments described herein and delivering the data to an external data receiving and processing device adapted to receive and analyze the data and provide a display of the data graphically or in various other forms. In other embodiments, the data is stored and displayed and analyzed later. The method includes obtaining data by measuring the exact angle, yaw, location and pitch of multiple body parts in time as well as the acceleration and other movements of the body parts by positioning the IMU's in appropriate locations along the seams and by positioning the seams at appropriate locations along the wearer's body. The method includes wirelessly or otherwise transmitting the data to an external data receiving and processing device that includes a processor. The external data receiving and processing device may control another electronic device and/or provide feedback based on the data analysis. Various algorithms and methods such as Kalman filtering, also known as linear quadratic estimation (LQE), may be used to analyze the data and present the data in a useful and user-friendly format.

FIG. 1 shows a garment 2 which is a pair of pants in the illustrated embodiment. In other embodiments according to various aspects of the disclosure, garment 2 can be any other garment, i.e. a shirt or other piece of apparel such as may be worn by a human, other animal or such as may be placed upon a movable device. In the illustrated embodiment, garment 2 includes seams 4 at least at outer lateral locations 6 and medial internal locations 8 on each pant leg 10. Seams 4 generally extend along the longitudinal direction of a wearer's legs and are therefore generally parallel to the wearer's femur in upper portion 14 of pant leg 10 and parallel to the wearer's tibia and fibula in lower portion 16 of pant leg 10, when garment 2 is worn by a wearer.

An advantage of the wearable activity monitor of the disclosure is that the electronic components that form the wearable activity monitor are disposed within, i.e. inside seams 4 and therefore not visible. Stated alternatively, the electronic components that form the wearable activity monitor are surrounded by fabric and inside a garment seam. A seam may be a portion of a garment in which two overlapping portions of fabric are joined together but the disclosed system may be formed in other types of garment seams in other embodiments. A close-up of seam 4 is shown in FIG. 1A. Seam 4 shown in FIGS. 1 and 1A represents one seam embodiment but various types of seams are used in other embodiments. Various stitching types and other methods may be used to form seams in other embodiments. In some particularly advantageous embodiments, garment 2 is a pair of denim jeans but other materials and other garments are used in other embodiments. In other embodiments, garment 2 may be an item of apparel worn by a wearer including but not limited to shorts, a shirt, a full body suit, sleeves for legs and arms and the like. Garment 2 may be formed of denim, stretch denim or various other suitable materials.

The garment is advantageously a tight fitting or form fitting garment so that the inertial measurement units, IMU's or other sensors disposed within the seams are accurately positioned with respect to a wearer's body.

FIG. 1A shows seam 4 formed of two fabric pieces 20, 22. The two fabric pieces 20, 22 may be joined together to form seam 4 by stitchings 26. Completely inside seam 4 and shown in dashed lines are sensors 30 and flexible connector 32. Sensors 30 may be inertial measurement units, IMU's or other sensors, and other components. In various embodiments, sensors 30 may be accelerometers, gyrometers, magnetometers, or other suitable motion sensors and in some embodiments, complementary accelerometers may be used. Sensors 30 are in electronic communication with one another and at least one microcontroller and with one or more external data receiving and processing devices. In some embodiments, sensors 30 are disposed on a connective ribbon or coupled together by other flexible connectors such as wires, fibers and the like. The flexible connectors 32 are also disposed within seam 4 and are long thin ribbon members such as will fit in a conventional garment seam. In some embodiments, a flexible circuit board such as a kapton board (or "kapton ribbon") is used as flexible connector 32. Kapton is a polyimide film developed by DuPont in the late 1960s that remains stable across a wide range of temperatures and is commonly used in flexible printed circuits, among other things. In other embodiments, other flexible types of circuit boards and other types of flexible plastic materials and/or flexible insulating materials in ribbon or other form, or various suitable connectors may be used. In other embodiments, flexible connector 32 can be formed by other flexible material such as textiles, conductive yarns or other suitable material. Flexible connector 32 may be a ribbon including multiple electrical connections and forming a communication bus. Multiple sensors 30 are coupled to flexible connector 32 as will be described in further detail below.

Figure 2:
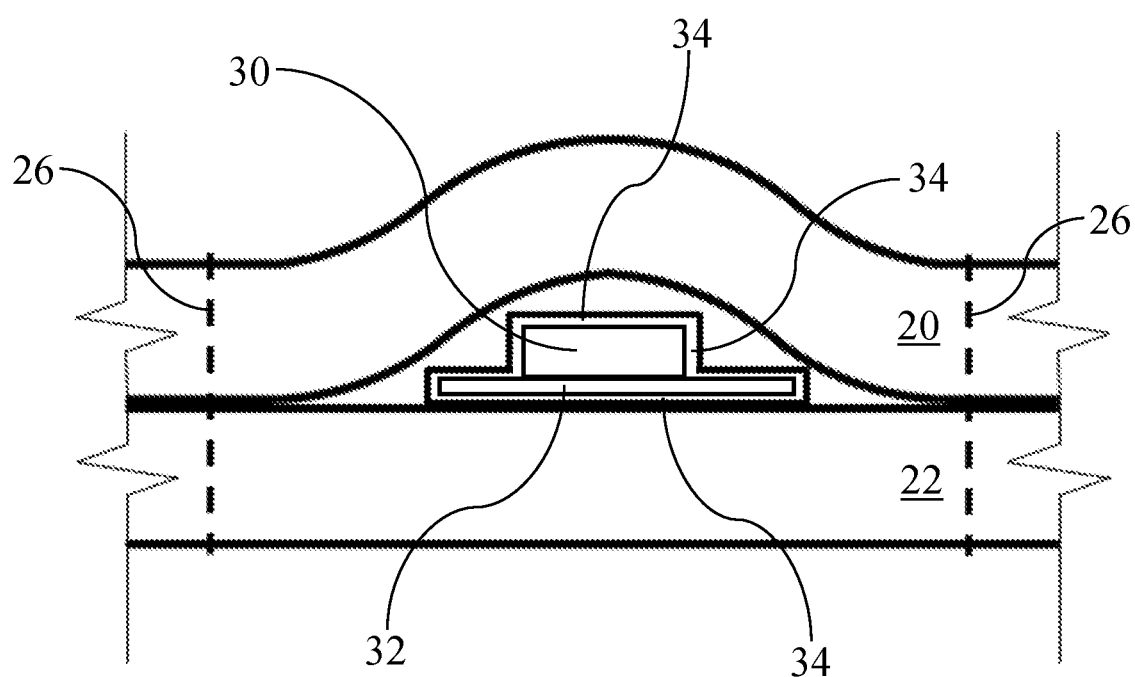
FIG. 2 shows a cross-sectional view of a seam of a wearable activity monitor garment according to various embodiments of the disclosure.

FIG. 2 shows a cross-sectional view of seam 4 such as shown in FIGS. 1 and 1A. Sensors 30 and flexible connector 32 are positioned inside seam 4 formed of fabric pieces 20, 22. Sensors 30 and flexible connector 32 are also advantageously coated with a waterproof coating 34 in various embodiments. In some embodiments, flexible connector 32 is formed of a waterproof material encasing the electrical connections and only the sensors 30 are coated with waterproof coating 34. Various suitable materials such as resin coatings used for isolating electronics or cold molding with materials such as commercially available Acrylonitrile Butadiene Styrene (ABS) resin which is a plastic, may be used as waterproof coating 34. In other embodiments, materials such as other thermoplastics, for example polyamide-6-6, PA66 (i.e. nylon66) may be used. In still other embodiments, other suitable materials may be used as a waterproof coating 34.

Figure 3A:
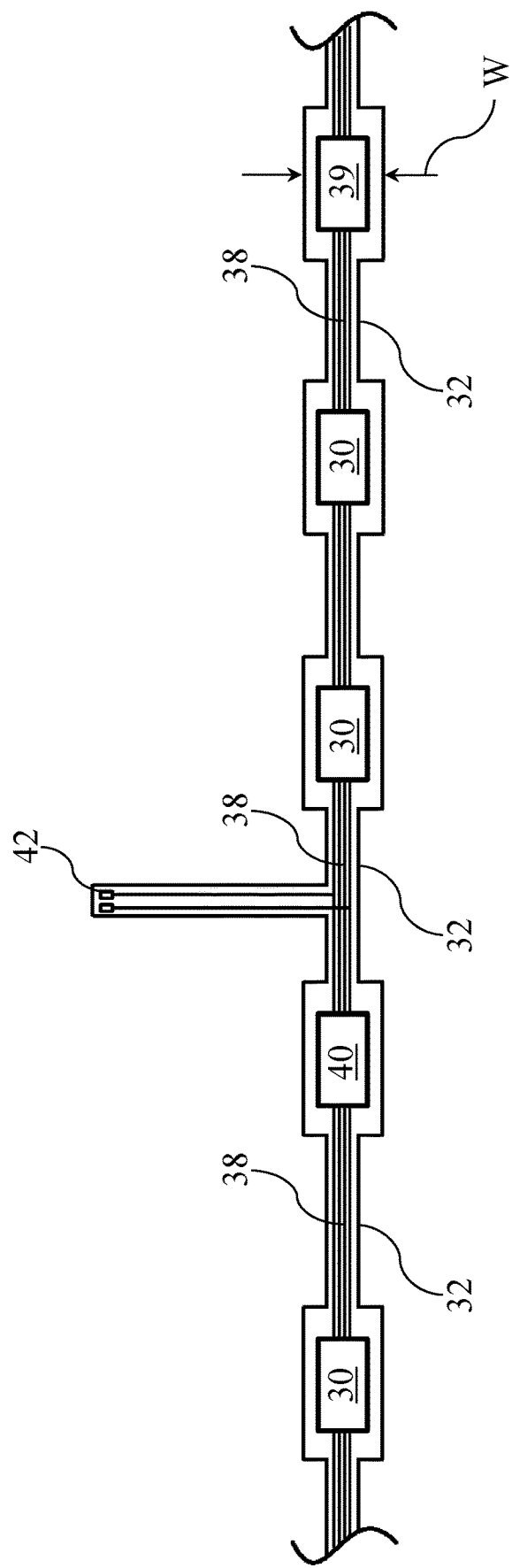
FIG. 3A shows inertial measurement units, IMU's, coupled together by a flexible connector disposed within a seam of the wearable activity monitor garment according to various embodiments of the disclosure.

Some details of flexible connector 32 and the sensors 30 disposed on flexible connector, are shown in FIG. 3A. FIG. 3A shows a motion capture circuit comprising a plurality of sensors 30 joined to flexible connector 32. In some embodiments, the flexible connector 32 and sensors 30 arrangement, may include a width W no greater than 1.5 cm but other suitable widths are used in other embodiments such that flexible connector 32 is disposed inside garment seam 4. Sensors 30 may be inertial measurement units, IMU's such as accelerometers, gyrometers and magnetometers but other sensors may be used in other embodiments. Accelerometers and gyrometers are known to indicate acceleration and angular velocity, respectively and can therefore be used to accurately indicate motion and can provide motion capture functionality. Magnetometers may function essentially as compasses that provide directional information with respect to the Earth's magnetic field. Magnetometers are useful, especially in conjunction with accelerometers and gyrometers, to provide location information including absolute orientation. Sensors 30 are electrically coupled to one another and other components, such as by conductive elements 38 (for example traces, wires, etc.) on flexible connector 32 but other means for electrical connection are used in other embodiments. Various suitable conductive materials may be used. For example, the flexible connector 32 may comprise a plurality of electrical cables 38, which may be coaxial cables in some embodiments.

In some embodiments, the IMU's, i.e. sensors 30 may be islands of electronics, formed on ordinary PCB's, and connected to each other by ribbons 32 that may be elastically stretchable flexible connectors. In particular, with respect to FIG. 3B and FIG. 3C, an elastically stretchable bus comprising a ribbon 32 provided with a couple of electrical cables 38 is shown. The electrical cables 38 are arranged along a crooked path (i.e. a continuously nonlinear path), such as a wavy (undulating) or a zigzag path. The ribbon 32 shown in FIG. 3B has an elastic stretchability less than the stretchability of ribbon 32 shown in FIG. 3C, so that for a given length of the ribbon 32, the electrical cables 38 of FIG. 3C can have a longer length than the embodiment of FIG.

3B. In other words, for a given length of ribbon 32, electrical cables 38 shown in FIG. 3C allow for greater stretching. The electric cables 38 tend to follow a more crooked path in a relaxed position, i.e. in absence of a stretching force, than when a stretching force is applied. In other words, when a stretching force is applied to the ribbon 32, the electric cables 38 follow a path which is more linear in shape, i.e. the electric cables 38 straighten out. In general the ribbon 32 is elastically stretchable by at least 10%. For example, the ribbon 32 may be formed of textile comprising stretchable yarns coupled to the electrical cables 38 by weaving.

Figure 3B:
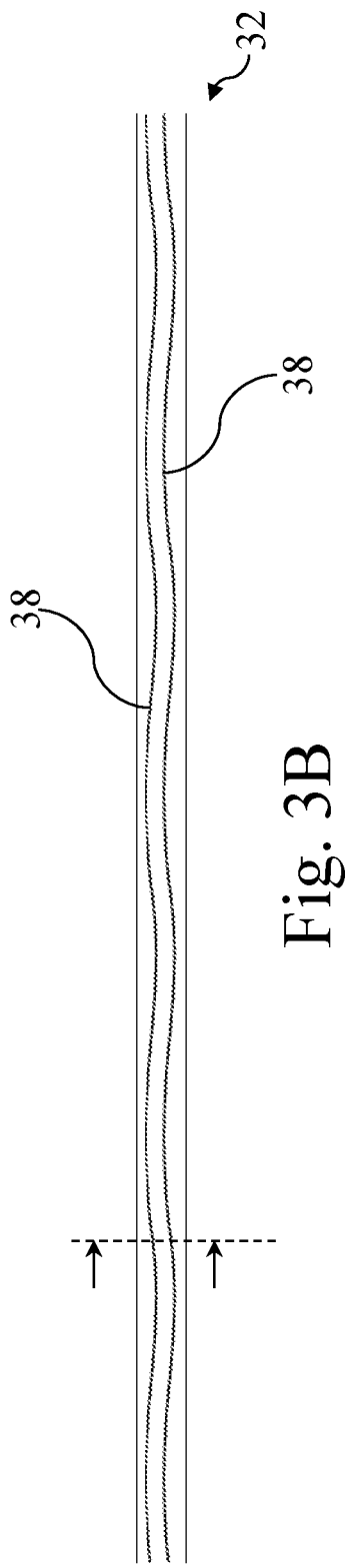
FIGS. 3B and 3C show an elastically stretchable ribbon forming a communication bus for the IMU's according to various embodiments of the disclosure.
Figure 3C:
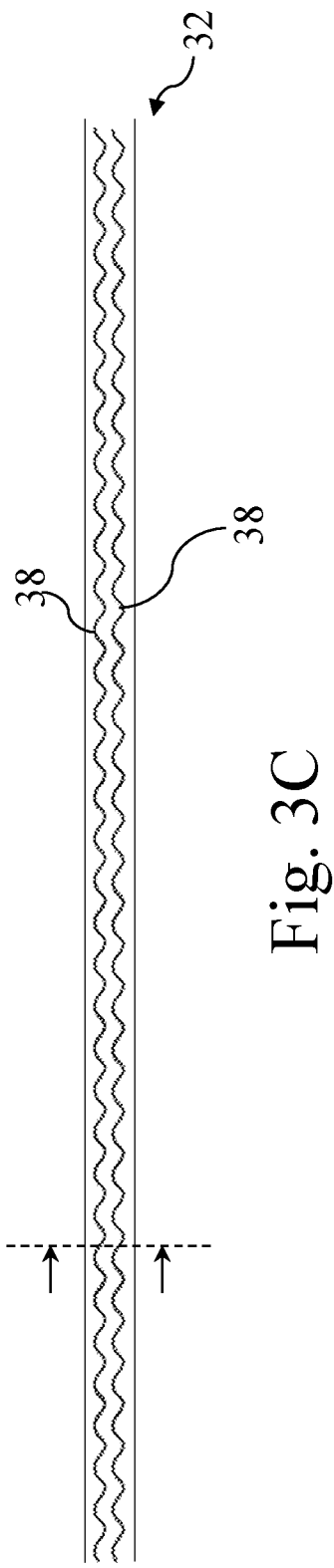
Figure 3D:
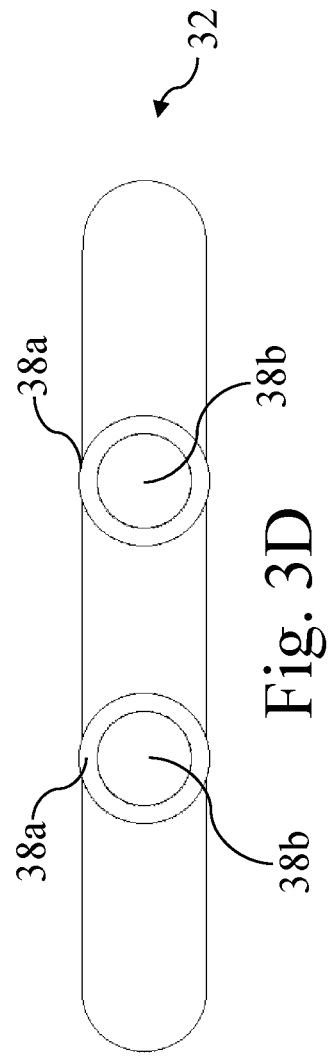
FIG. 3D shows a cross-sectional view of the elastically stretchable ribbons of FIGS. 3B and 3C.

In FIG. 3D a cross-section view of the ribbon 32 shown in FIGS. 3B and 3C is shown. In this embodiment the electrical cables 38 are coaxial cables having an outer conductor 38a and an inner conductor 38b. For example, a coaxial cable 38 can be used for connecting IMU's or other electronic component to a power supply, the other coaxial cable 38 can be used for transmitting data.

In addition to sensors 30, FIG. 3A also shows microcontroller 40 disposed on flexible connector 32. Various microcontrollers are used. In other embodiments, microcontroller 40 may be disposed at various other locations in or on garment 2. In some embodiments, the microcontroller may be disposed as a button over the fly of the jeans or on a belt loop, but the microcontroller may be disposed at any of various other suitable locations. In various embodiments, flexible connector 32 has Bluetooth circuitry as well as microcontroller 40. In various embodiments, microcontroller 40 includes a radio antenna that wirelessly transmits the data obtained from sensors 30. The Bluetooth circuitry enables the components on the flexible connector 32 and flexible connector 32 itself to communicate to external data receiving and processing devices such as computers, tablets, cellular telephones, or other personal electronic devices or processors. The Bluetooth circuitry includes various suitable wireless transmission devices such as radio antennas to transmit the data wirelessly or otherwise to one or more external components.

Referring again to FIG. 3A, relative widths of flexible connector 32 and sensors 30 may vary according to other embodiments. In some embodiments, flexible connector 32 includes enlarged platform sections to accommodate sensors 30 and in other embodiments, flexible connector 32 includes a constant width. Flexible connector 32 and therefore sensors 30 may be connectable to outside electronic devices using terminals 42. In some embodiments, terminals 42 may be used to connect flexible connector 32 to a power source, battery or battery charger, or other electronic device. In some embodiments, microcontroller 40 includes a battery that may be a rechargeable battery and according to such embodiments, terminals 42 may provide connection to a battery charger. In some embodiments, terminals 42 may provide connection to a wireless transmitter such as may be positioned outside the seam, in some embodiments. In some embodiments, a tactile or visual feedback device 39 is present to provide feedback to the wearer. Feedback device 39 may be a light emitting diode, LED device in some embodiments and in other embodiments, feedback device 39 may be a vibrational member used to provide tactile feedback to the wearer. According to various other embodiments, flexible connector 32 may include additional components also disposed within seams 4.

In some embodiments, terminals 42 may provide connection to a computer or other processor such as may be used to program microcontroller 40 and/or update firmware for microcontroller 40.

FIG. 4A presents one embodiment of locations of sensors within seams 4, according to various aspects of the disclosure. In FIG. 4A, sensor locations 44 are on seam 4 of upper portion 14 of pant leg 10 and sensor locations 46 are on seam 4 of lower portion 16 of pant leg 10. FIG. 4A shows two sensor locations, 44 and 46 on outer lateral locations 6 and also two sensor locations 44, 46 on medial internal locations 8 on each pant leg 10 but various other locations and arrangements may be used in other embodiments. In some embodiments, at each sensor location 44, 46 there are three sensors—an accelerometer, a gyrometer and a magnetometer, but other types and numbers of sensors may be used at the sensor locations, in other embodiments. Furthermore, in other embodiments, other sensor locations are used. For example, an accelerometer, gyrometer, and magnetometer may be positioned very close to one another at any of various other locations along upper portion 14 of garment leg 10 and in other embodiments, the accelerometer, gyrometer, and magnetometer may be positioned apart from one another at various locations but each along upper portion 14 of pant leg 10. The same is true for the positioning of sensors 30 along lower portion 16 of pant leg 10. In some embodiments, an accelerometer, gyrometer, and magnetometer may be positioned in close proximity to one another at any of various locations along lower portion 16 such as at sensor location 46 and in other embodiments, the accelerometer, gyrometer, and magnetometer or other suitable sensors 30, may be spaced apart from one another at various locations along lower portion 16.

The disclosure provides for obtaining data by using the aforementioned sensors to measure the exact angle, yaw, location and pitch of multiple body parts in time as well as the acceleration and other movements of the body parts by positioning the IMU's or other sensors in appropriate locations along the seams and by positioning the seams at appropriate locations along the wearer's body. Graph 48 shown in FIG. 4A illustrates an example of three data curves 51, 52, 53 such as may be obtained from three sensors at sensor location 44.

FIG. 4A shows a further sensor location 45 on waist location 7. In this embodiment, the garment may include a waist seam 4 extending along the wearer's waist. The waist seam 4 includes at least one IMU 30 disposed along the waist location 7, preferably at the wearer's lower back when worn.

The IMU 30 disposed at the location 45 may be used for detecting the gravity vector so that the angle, yaw, location and pitch of multiple body parts can be obtained by taking the gravity vector detected at location 45 as reference.

Figure 4C:
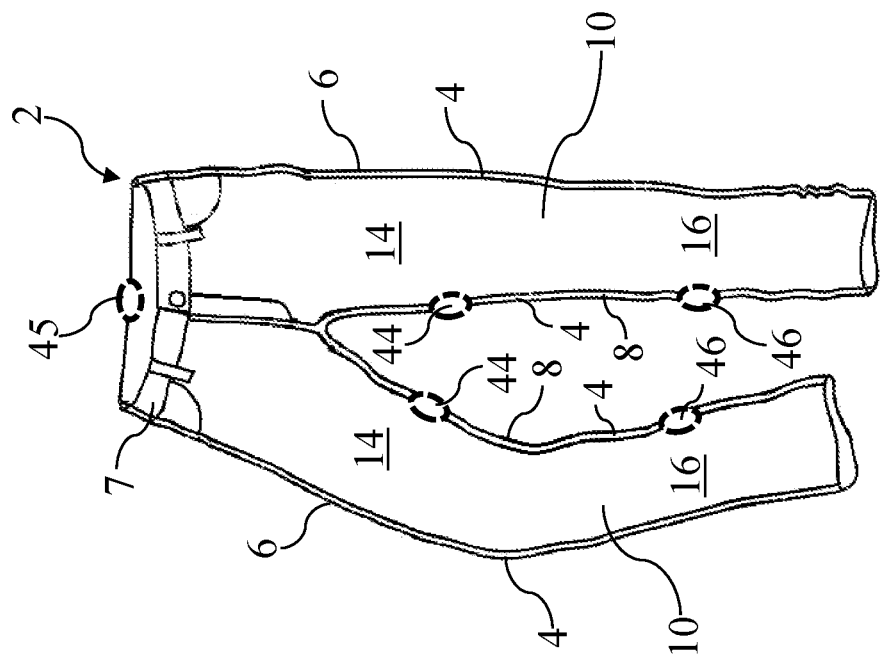
Figure 4B:
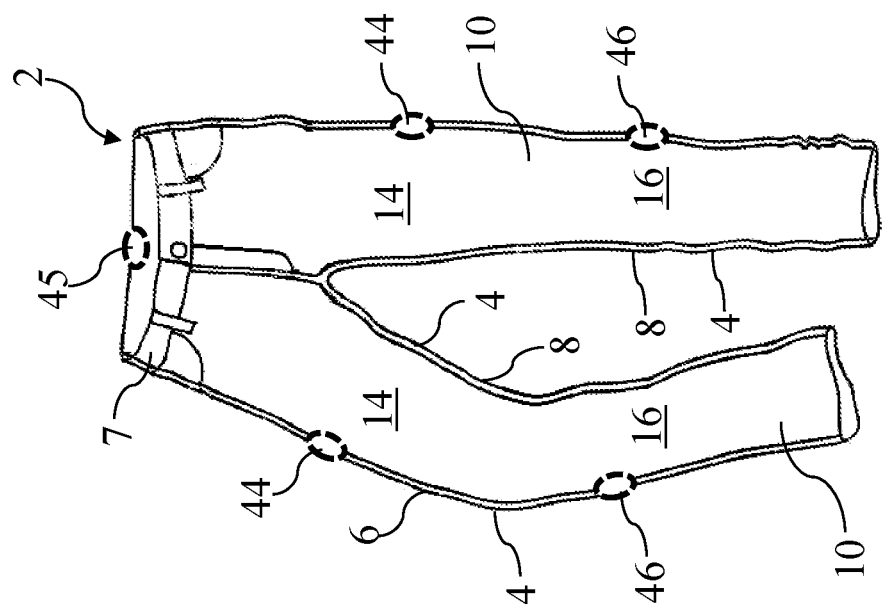

FIGS. 4B and 4C illustrate two other embodiments of the arrangement of motion sensors within seams 4, according to the disclosure. In FIG. 4B, only one sensor location 44 is present along upper portion 14 of garment leg 10 and only one sensor location 46 is present along lower portion 16 of garment leg 10. Each of the sensor locations 44, 46 is on outer lateral locations 6 of pant leg 10 in FIG. 4B. In contrast, in FIG. 4C, only one sensor location 44 is present along upper portion 14 of garment leg 10 and only one sensor location 46 is present along lower portion 16 of garment leg 10 but each of the sensor locations 44, 46 is located at medial internal locations 8 of pant leg 10.

In general, in the case of a pair of pants, the seams 4 of the garment 2 include, for each pant leg 10 of the pair of pants, an outer lateral seam 4 extending in a longitudinal direction along a wearer's leg and/or an inner medial seam 4 extending in the longitudinal direction along the wearer's leg. Each of the outer lateral seam 4 and/or each of inner medial seams 4 include at least one IMU 30 disposed along a wearer's femur and at least one IMU 30 disposed along a lower portion 16 of the wearer's leg.

Various other numbers of sensors and locations in addition to those shown in FIGS. 4A-4C, can be used and the sensors can be variously positioned in various embodiments.

Figure 5:
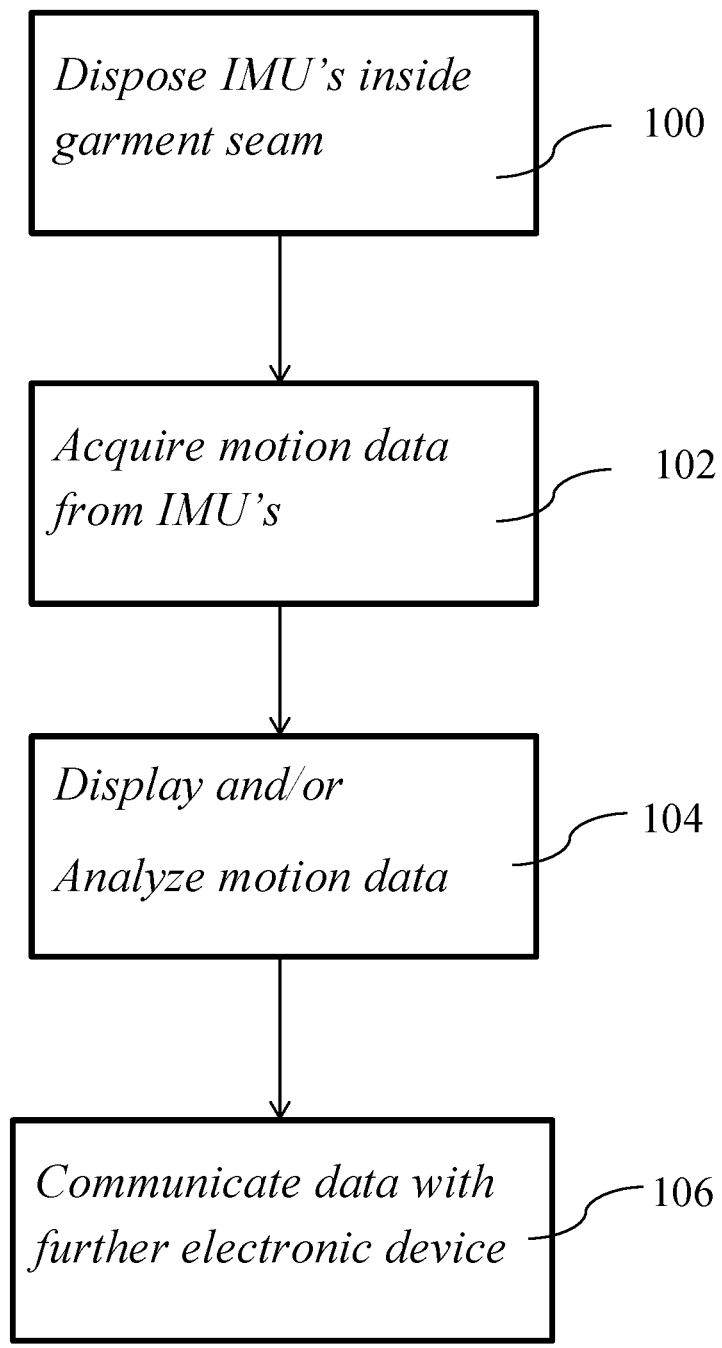
FIG. 5 is a flow chart illustrating a method according to various embodiments of the disclosure.

The disclosure provides a system and method in which the motion and orientation information is wirelessly transmitted such as by microcontroller 40 shown in FIG. 3A or another suitable wireless transmission device disposed on or in the garment. Referring to FIG. 5, the method for monitoring and analyzing real time motion may comprise: disposing a plurality of inertial measurement units (IMU's) within seams of a garment disposed on a non-stationary entity (step 100) as described above; acquiring motion data from the plurality of inertial measurement units (IMU's) (step 102) as described above; and displaying and/or analyzing the data (step 104) as described herein. The movement associated with the motion data may be presented on a visual display. The method may also include communicating the motion data to another electronic device (step 106).

Figure 6:
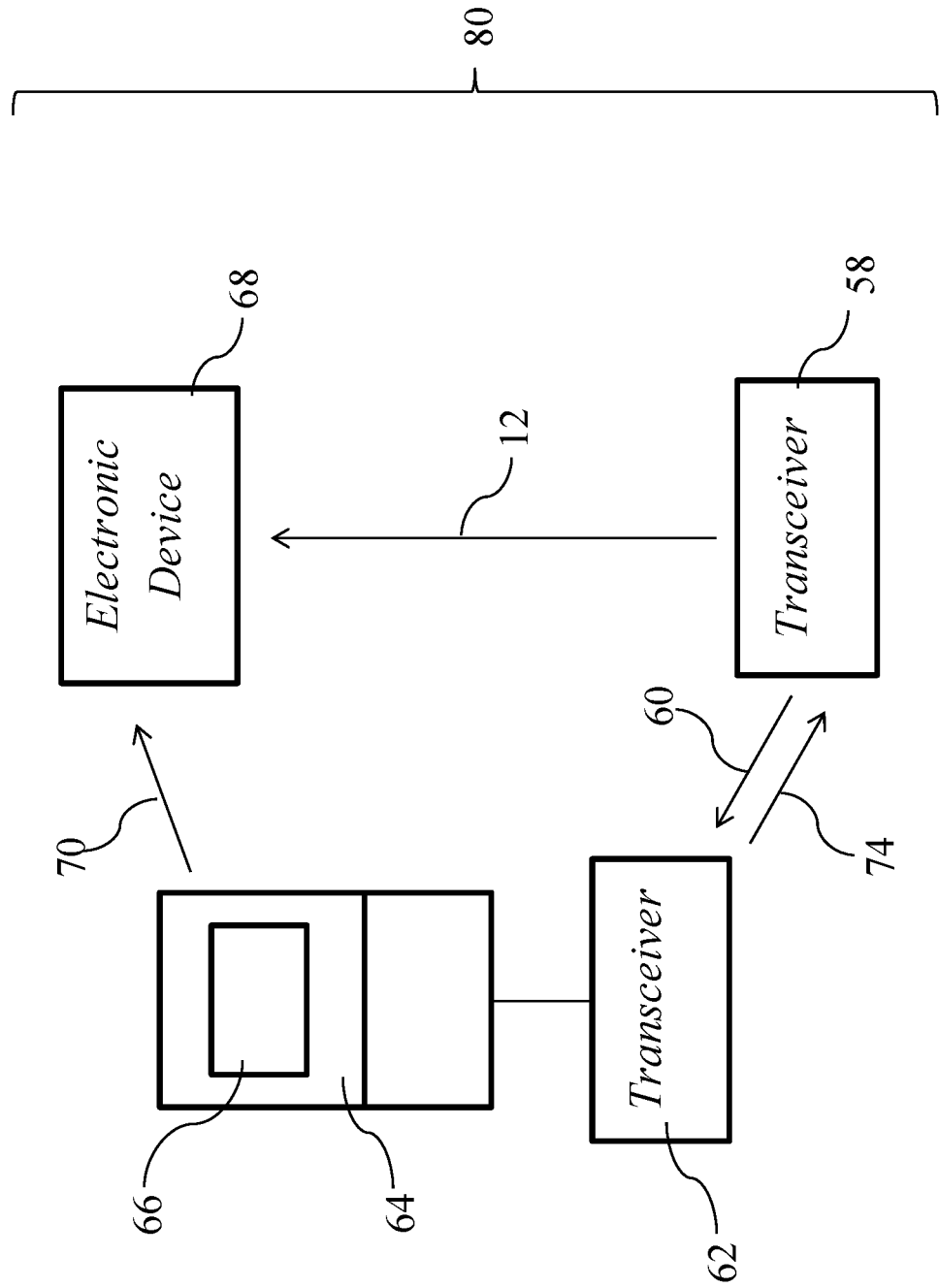
FIG. 6 is a schematic representation of a motion capture system according to various embodiments of the disclosure.

FIG. 6 shows a motion capture system 80 according to an embodiment of the present invention, including wireless transceiver 58 associated with garment 2, transmitting data 60 to a transceiver 62 associated with an external device 64 including a processor adapted to receive and analyze the transmitted data and a display 66 that displays the data. In some embodiments, motion capture system 80 also includes another electronic device 68 such as described below. In various embodiments, the wireless transmission device disposed on or in garment 2 may additionally include both a transmitter and receiver and serve as wireless transceiver 58. Wireless transceiver 58 may communicate using Bluetooth (BT), Bluetooth Low Energy (BLE), or other suitable wireless radio technology communication modules. External device 64 may be or may include a computer, various processors and other data analysis features. In some embodiments, external device 64 is a tablet or cellular telephone or other personal electronic device. Display 66 may display the analyzed data in many formats such as a graphically or in table form. In various advantageous embodiments, display 66 presents the data in a visual form that shows the real time motion of the wearer of the garment. External device 64 may include a GUI for the user to use to analyze, manipulate and display the data. In various embodiments, external device 64 may analyze and display the data in real time and also include a memory such that the data may also be stored and analyzed and displayed at a later time when so desired.

Figure 7:
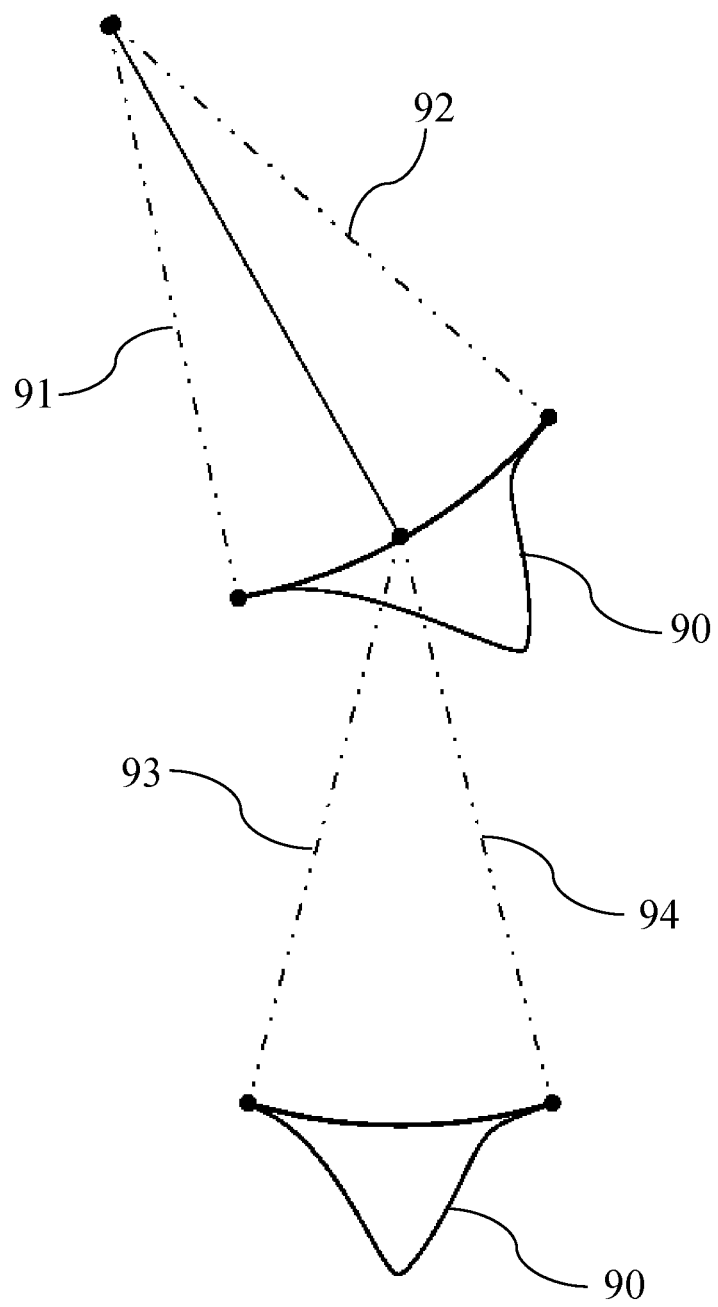
FIG. 7 shows a graphic representation of the motion data collected and displayed according to a particular embodiment of the present invention.

In some embodiments, the step 104 of displaying and analyzing may comprise a step of collecting the motion data during a collecting period and a step of displaying the collected data when desired. The collected data may be displayed graphically as shown in FIG. 7 although other displays may be presented in other embodiments. In particular, the external device 64 may analyze the collected data and display the statistic distribution 90 (for example a histogram) of the angles for each human wearer's femurs and for each human wearer's tibias or fibulas. For example, the motion data collected may be displayed with a plurality of segments 91-94 arranged at angles corresponding to the minimum and maximum angles collected for femur (91, 92) and tibia (93, 94) of each leg. FIG. 7 shows a graphic representation of the collected motion data of a leg (for example the right leg). In particular, segments 91 and 92 represent the minimum angle and maximum angle achieved by the femur during the collecting period. Segments 93 and 94 represent the minimum angle and maximum angle achieved by the tibia during the collecting period.

The user can switch between the display relating the motion data of a leg to the other leg by means of a graphical user interface, so that possible asymmetries of movements can be displayed graphically in a simple and intuitive manner for the user.

Various methods and algorithms may be used to process and analyze the transmitted motion and location data and to present a display or otherwise present the data in a useful form. In some embodiments, Kalman filtering may be used. Kalman filtering, also known as linear quadratic estimation (LQE), is an algorithm that uses a series of measurements observed over time, containing statistical noise and other inaccuracies, and produces estimates of unknown variables that tend to be more precise than those based on a single measurement alone, by using Bayesian inference and estimating a joint probability distribution over the variables for each timeframe.

The Kalman filtering embodiment is presented by way of example only and in various embodiments, various data analysis and presentation methods are used. In various embodiments, multiple garments 2 transmit data to an external device such as external device 64 and the data processing and analysis may include a comparison of data received from multiple wearers.

Referring again to FIG. 6, in some embodiments, external device 64 uses the data received and processed, to control another electronic device 68 such as by way of signal 70. In some embodiments, electronic device 68 is a gaming device and in other embodiments, electronic device 68 may be a home or automotive appliance, computer game, a video game console, or it may represent any of various other applications of an electronic device capable of receiving a signal, either wirelessly or otherwise transmitted from external device 64, and being controlled by such signal. Various games that are played based on wearer movements, can be implemented and these include games both on mobile devices or other platforms. In other embodiments, the system including garment 2 as described above, may communicate directly with electronic device 68. According to this embodiment, data signals 72 are transmitted directly by a wireless transmitter such as transceiver 58, to the electronic device and in various embodiments, multiple garments to may communicate directly with electronic device 68.

In various embodiments, the system may also provide an auditory, visual or other emergency alarm. In some embodiments, various movements or movement patterns such as excessive spinning, high impact or unmitigated freefall, or various other movements or more patterns, may trigger an emergency alarm. In some embodiments various other forms of visual and/or tactile feedback, i.e. non-emergency notifications, may be provided to the user. The alarm or other notification may be presented visually such as on various displays such as may be on external device 64. In other embodiments, the alarm or notification may be a tactile notification such as vibration on a wearable device such as a cellular telephone with a vibration engine. In some embodiments a light emitting diode, LED, or vibrational member within the seam (see feedback device 39 in FIG. 3A) of the garment itself, is used to convey the alarm or other notification via visual and/or tactile feedback to the user. The notification of the emergency situation or other feedback may be obtained by external device 64 and provided as signal 74 to transceiver 58. In some embodiments, microcontroller 40 generates the notification and sends the same to the LED or vibrational member within the seam.

The visual or tactile feedback may be a single or multiple vibrational beeps (i.e., "veeps") or single or multiple LED flashes to inform the user that the garment is turned on, that the garment is in its reduced set of functions, that the garment is in full monitoring function, and so forth.

Some embodiments may provide that a feedback notification may be obtained by the external device 64 on the basis of the motion data acquired by the IMU's. The feedback notification may provided as signal 74 to transceiver 58, so that microcontroller 40 generates the notification and sends the same to the feedback device 39 (LED or vibrational member) within the seam. In some embodiments, the feedback device 39 may comprise a plurality of vibrational members arranged within the seam of the garment at different positions associated to particular parts of the wearer's body, so that a tactile feedback may be provided to one or multiple different parts of the wearer's body at the same time, in response to the motion data acquired by the IMU's and analyzed by the external device 64. For example, the tactile feedback can be used for notifying to the wearer wrong and/or correct movements of wearer's body parts during physical exercises.

In some embodiments, external device 64 may provide firmware updates received by wireless transceiver 58.

The disclosed garment and system enables the data to be analyzed and used for various advantageous purposes and applications. In some embodiments, the disclosed system provide for monitoring more than one garment such as two garments worn by a wearer, e.g, a pair of pants and an upper body garment. In one embodiment, the disclosed garment and system provide for monitoring group sports activities. For example, a single trainer can simultaneously check on multiple sportsmen to determine if, for example all the students are doing the right thing when they go through their training moves, or for comparative purposes. This can be done realtime or later off-line as the memory required to store the data is small in size and a trainer can later compare data among subjects and make various determinations. In other embodiments, the advantage of injury prevention is achieved by analyzing the movement of an athlete or other performer, for example. The motion data may be used for running or walking style and balance analysis. The data can demonstrate which leg is used more and whether the wearer's steps are equal over time. Gait analysis can also be used to suggest anatomical corrections and to determine a proper style of shoe, such as a running shoe. Various other types of activity tracking can be achieved. Sleep behavior can also be monitored based on the data analysis.

In some embodiments, the data can assist in calculating calories burned based on an integral of the sensor data and body measurements such as height, weight, leg length and the like. In still other embodiments, a performer such as a dancer or an athlete such as a skier or a skateboarder can develop a particular move and record the captured data provided by the disclosure instead of having to review a lengthy video that may include many irrelevant details.

The preceding merely illustrates the principles of the disclosure. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

The invention claimed is:

1. A motion capture circuit comprising a ribbon of a flexible material, a plurality of electrical connections forming a communication bus, a plurality of inertial measurement units (IMU's) electrically coupled to one another by said electrical connections along said ribbon, a microcontroller electrically connected with said plurality of IMU's, and a wireless transmitter adapted to wirelessly transmit data from said IMU's to at least one external data receiving and processing device, said wireless transmitter further comprises a wireless receiver capable of receiving data from said at least one external data receiving and processing device, said at least one external data receiving and processing device adapted to control at least one further electronic device based upon said data, said further electronic device being chosen from a gaming device, a home or automotive appliance, a computer game, a video game console or any other applications of an electronic device capable of receiving a signal, wherein said ribbin is elastically stretchable by at least 10%, said plurality of electrical connections being arranged along said ribbon in a crooked path, wherein said ribbon is formed of a textile comprising stretchable yarns coupled to the electrical connections by weaving, wherein the motion capture circuit is configured to be contained within a seam of a pair of pants, said sems including for each pant leg of said pair of pants an outer lateral seam extending in a longitudinal direction and/or an inner medial seam extending in said longitudinal direction, each of said outer lateral seams and/or each of said inner medial seams including at least one of said plurality of IMU's disposed along a pant leg portion corresponding to the human wearer's femur and at least one of said plurality of IMU's disposeed along a pant leg portion corespondint to the human wearer's tibia and biula, and parallel to the wear's tibia and fibula, wherein said processor is configured for analyzing motion data regarding angle, yaw, pitch, location and acceleration of the human wearer's femurs and said human wearer's tibias and fibulas.

2. The motion capture circuit according to claim 1, further comprising a waterproof coating on said IMU's and said ribbon, said waterproof coating being produced by a low pressure molding process.

3. The motion capture circuit according to claim 1, further comprising at least one of an LED and a vibration member electrically connected to said plurality of IMU's and said wireless receiver by said ribbon.

4. The motion capture circuit according to claim 1, wherein said at least one external data receiving and processing device analyzes the collected data and display a statistic distribution of the angles for each human wearer's femurs and or each human wearer's tibias or fibulas.

5. The motion capture circuit according to claim 1, wherein said at least one external data receiving and processing device analyzes the collected data and display the minimum angle and maximum angle achieved by each human wearer's femurs and or each human wearer's tibias or fibulas.

6. A motion capture circuit comprising a ribbon of a flexible material, a plurality of electrical connections forming a communication bus, a plurality of inertial measurement units (IMU's) electrically coupled to one another by said electrical connections along said ribbon, a microcontroller electrically connected with said plurality of IMU's and a wireless transmitter adapted to wirelessly transmit data from said IMU's to at least one external data receiving and processing device, said wireless transmitter further comprises a wireless receiver capable of receiving data from said at least one external data receiving and processing device, said at least one external data receiving and processing device adapted to control at least one further electronic device based upon said data, said further electronic device being chosen from a gaming device, a home or automotive applicance, a computer game, a video game console or any other applications of an electronic device capable of receiving a signal, wherein said ribbon is elastically stretchable by at least 10%, said plurality of electrical connections being arranged along said ribbon in a crooked path, and wherein said ribbon is formed of a textile comprising stretchable yarns coupled to the electrical connections by weaving, wherein the motion capture circuit is configured to be contained within a seam of a pair of pants, said seams including for each pant leg of said pair of pants an outer lateral seam extending in a longitudinal direction and/or an inner medial seam extending in said longitudinal direction, each of said outer lateral seams and/or each of said inner medial seams including at least one of said plurality of IMU's disposed along a pant leg portion corresponding to the human wearer's femur and at least one of said plurality of IMU's disposed along a pant leg portion corresponding to the human wearer's tibia and fibula, and parallel to the human wearer's tibia and fibula, wherein said processor is configured for analyzing motion data regarding angle, yaw, pitch, location and acceleration of the human wearer's femurs and said human wearer's tibias and fibulas, wherein said external device is configured to analyze the motion data and display a statistic distribution of the angles for each human wearer's femurs and or each human wearer's tibias or fibulas, and wherein said at least one external data receiving and processing device is configured to analyze the motion data and display a minimum angle and maximum angle achieved by each human wear's femurs and or each human wearer's tibias or fibulas.

* * * * *